United States Patent [19]

Seifert et al.

[11] Patent Number: 5,168,873

[45] Date of Patent: Dec. 8, 1992

[54] METHOD AND APPARATUS FOR FIBER OPTIC SENSOR INSERTION

[75] Inventors: George P. Seifert, Shoreview, Minn.; Jeffrey A. Schweitzer, St. Paul; Jerome T. Hartlaub, New Brighton, both of Minn.

[73] Assignee: Medtronic, Inc., Minneapolis, Minn.

[21] Appl. No.: 516,623

[22] Filed: Apr. 30, 1990

[51] Int. Cl.⁵ .............................................. A61G 5/00
[52] U.S. Cl. .................................... 128/634; 128/664; 128/666; 356/41; 356/373; 356/375
[58] Field of Search ............... 128/633, 634, 637, 664, 128/666, 397, 398; 356/41, 51, 373, 375; 606/15, 17

[56] References Cited

U.S. PATENT DOCUMENTS

| | | | |
|---|---|---|---|
| 3,647,299 | 3/1972 | Lavellee | 356/41 |
| 4,114,604 | 9/1978 | Shaw et al. | 128/2 L |
| 4,295,470 | 10/1981 | Shaw et al. | 128/634 |
| 4,416,285 | 11/1983 | Shaw et al. | 128/634 |
| 4,623,248 | 11/1986 | Sperinde | 356/41 |
| 4,624,570 | 11/1986 | Bertellini | 356/373 |
| 4,651,741 | 3/1987 | Passafaro | 128/633 |
| 4,776,340 | 10/1988 | Moran et al. | 128/634 |
| 4,785,814 | 11/1988 | Kane | 128/634 |
| 4,986,663 | 1/1991 | Cecchi et al. | 356/373 |

Primary Examiner—David M. Shay
Attorney, Agent, or Firm—Harold R. Patton; Reed A. Duthler

[57] ABSTRACT

A system for insertion of a fiber optic diagnostic sensor into the human body. The sensor is of the type which functions by emission of light into the body and reception of light reflected from the body. In particular, the system is intended for use with fiber optic reflectance oximeters. The fiber optic sensor is inserted into an introducer catheter, and coupled to monitoring equipment and activated as the sensor is advanced through the introducer catheter. By appropriately filtering or otherwise processing the signal indicative of reflected light received by the sensor, its position relative to the end of the introducer catheter can be determined. This allows for accurate insertion of the fiber optic sensor, regardless of the length of the introducer catheter and regardless of the length and/or number of fittings or manifolds through which the fiber optic sensor must pass.

9 Claims, 8 Drawing Sheets

METHOD AND APPARATUS FOR FIBER OPTIC SENSOR INSERTION

BACKGROUND OF THE INVENTION

The present invention relates generally to medical sensors, and in particular to fiber optic sensors.

Fiber optic sensors, and in particular fiber optic reflectance oximeters, are well known to the art. One example of such a sensor is disclosed in U.S. Pat. No. 4,623,248 issued to Sperinde, which discloses a three wavelength reflectance oximeter. Typically, such sensors are introduced into the vascular system by means of an introducer catheter. Progress of the fiber optic sensor through the introducer catheter can be monitored by means of markings along the fiber optic sensor. However, in order for the markings to be meaningful, it is necessary that the total length of the introducer catheter be known, including al manifolds and fittings through which the sensor must pass. This length can then be compared to the markings on the fiber optic sensor to provide a rough guide as to the position of the distal end of the sensor.

Unless the fiber optic sensor, introducer catheter, and associated fittings and manifolds come as part of a packaged set, it is unlikely that the markings on the fiber optic sensor will line up precisely with the proximal end of the introducer catheter when the tip of the fiber optic sensor is properly positioned relative to the distal end of the introducer catheter. Preferably, the tip of the fiber optic sensor should extend somewhat (a few millimeters) from the end of the introducer catheter, but not an excessive distance.

SUMMARY OF THE PRESENT INVENTION

The present invention provides a method for monitoring the position of the diagnostic fiber optic sensor (hereafter "the sensor") within the introducer catheter (hereafter "the introducer") to provide an indication of when the tip of the fiber optic sensor passes through the distal end of the introducer and is located properly within the vascular system. The method employed comprises activation of the senor while still inside the introducer. Red or infrared light is emitted from the distal end of the sensor, and light reflected into the distal end of the sensor is monitored. The inventors have determined that the signal indicative of light reflected back into the distal end of the sensor displays consistent and measureable changes as the sensor passes through the distal end of the introducer allowing for an accurate determination of the position of the sensor.

The method is particularly valuable in that it may be practiced using monitoring equipment similar to that known to the prior art with some modifications. This provides a particularly convenient method for insertion of the sensor, as the same equipment used to monitor the sensor after insertion may be used to provide an indicator as to proper location of the sensor.

DETAILED DESCRIPTION OF THE INVENTION

Figure 1:
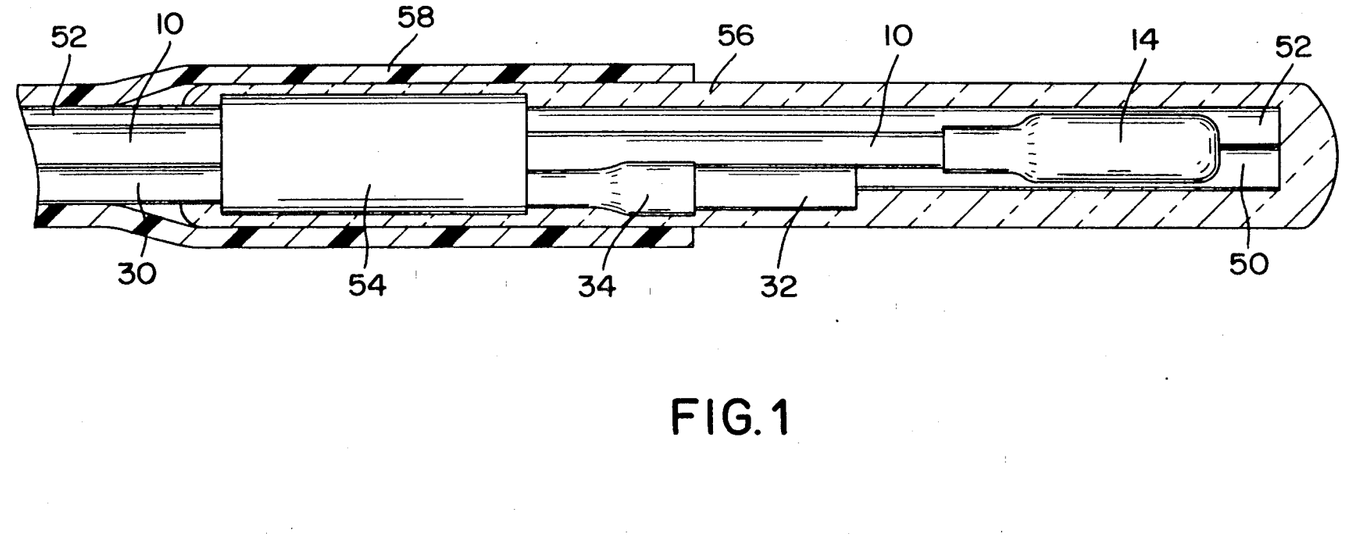
FIG. 1 is a side, cutaway view of the distal end of a fiber optic sensor appropriate for use in conjunction with the present invention.

FIG. 1 is a side, cutaway view of the distal end of a sensor appropriate for use in conjunction with the present invention. This sensor is described in more detail in the previously filed, copending patent application Ser. No. 07/314,615 for "BLOOD GAS MONITOR SENSORS", filed Jan. 23, 1989, by Schweitzer et al. This application is incorporated herein by reference in its entirety. This prior application discloses the details of construction of the pH sensor 32 and the $CO_2$ sensor 14 included in the lead illustrated in FIG. 1.

The pH sensor 32 is mounted to the end of an optical fiber 30 and retained by means of a sleeve 34. The $CO_2$ sensor 14 is mounted to the end of a second optical fiber 10. Optical fibers 50 and 52 function as the emitter fiber and receiver fiber, respectively, of a reflectance oximeter. Red and infrared light are applied to the proximal end of fiber 52 and emitted from the distal end of fiber 52. Reflected light enters the distal end of fiber 50 and is passed proximally to apparatus for monitoring the intensity of the reflected light. In general, apparatus such as that disclosed in the above-cited Sperinde patent will work appropriately to monitor the amplitude of reflected light in conjunction with the present invention. Alternatively, apparatus generally as disclosed in copending, commonly assigned patent application Ser. NO. 07/516,604, for a "FIBER-OPTIC OXYGEN SATURATION/HEMATOCRIT SENSOR", filed as of the date of the present application, by Seifert, Schweitzer and Proctor, and incorporated herein by reference or as disclosed in U.S. Pat. No. 4,776,340 issued on Oct. 11, 1988, to Moran et al, also incorporated herein by reference, may be employed.

The optical fibers 10, 30, 50 and 52 are bound together by an epoxy adhesive 54, and encapsulated in a transparent polyurethane coating 56. A heat-shrink sensor tube 58 serves to retain the fibers together, and extends back to optical couplers located at the proximal ends of each of the fibers.

While the distal ends of optical fibers 50 and 52 are shown as defining 90° angles with respect to the axis of the fibers, in some cases, it may be desirable to bevel the ends of these fibers at lesser angles in order to facilitate using the same fibers for transmitting and receiving functions, as disclosed in the above-cited Schweitzer et al application. However, when separate transmitting and receiving fibers are used as in the configuration illustrated in FIG. 1, a 90° angle is appropriate.

Figure 2:
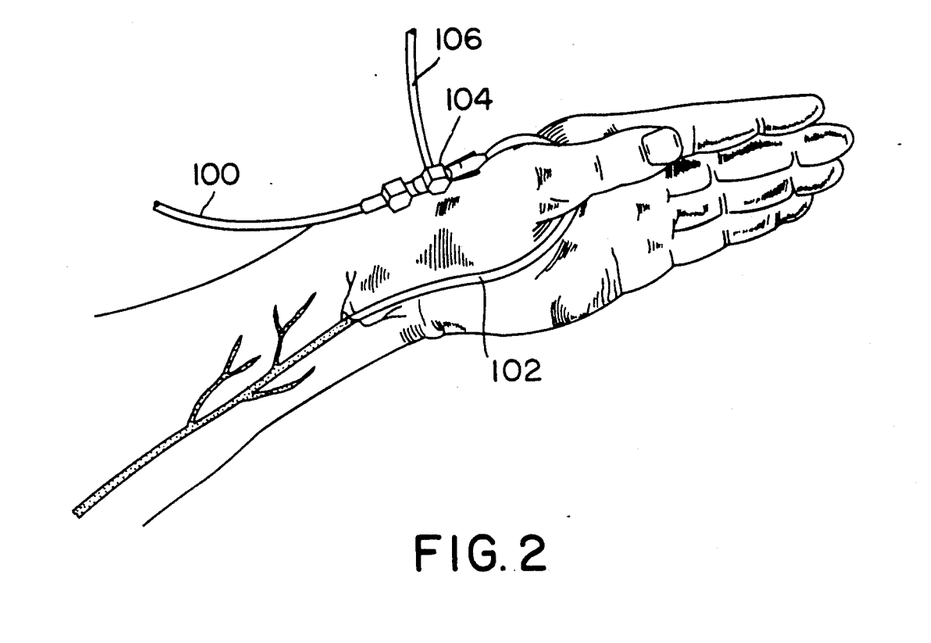
FIG. 2 is an illustration of the insertion of the sensor of FIG. 1 through an introducer into the vascular system.

FIG. 2 illustrates the insertion of the sensor 100 into the introducer 102. Coupled to the proximal end of the introducer 102 is a manifold 104, from which a pressure monitoring line 106 extends. The distal end of the introducer 102 is located within the venous system. It is desirable to advance the sensor 100 through the introducer 102 until its distal end protrudes slightly from the distal end of the introducer.

Figure 3:
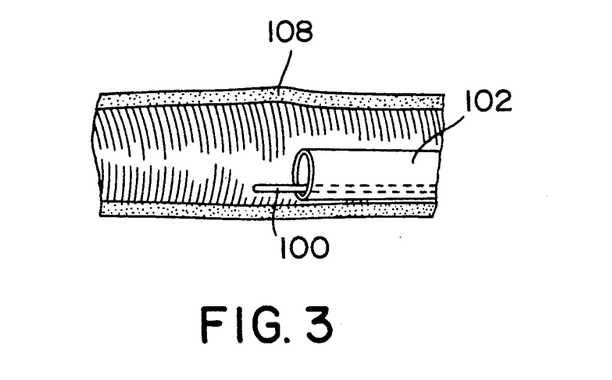
FIG. 3 is a side, cutaway view showing the proper location of the sensor when introduced into the vascular system.

FIG. 3 shows a side, cutaway view through the vein 108 in which the introducer 102 and the sensor 100 have been inserted. The sensor 100 preferably extends a few millimeters out of the distal end of the indicator 102 so that the sensor is exposed to the bloodstream, without optical interference from the end of the introducer 102, while still being maintained in proper orientation within the vein 108 by the introducer 102.

Figure 4A:
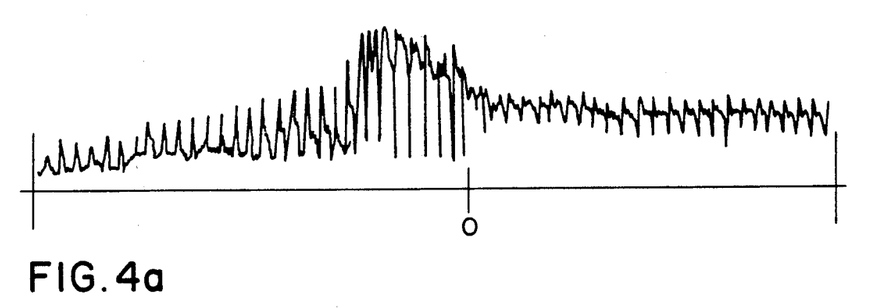
FIGS. 4A, 4B and 4C illustrate the signal indicative of light reflected back into the distal end of the sensor as it passes down the introducer.
Figure 4B:
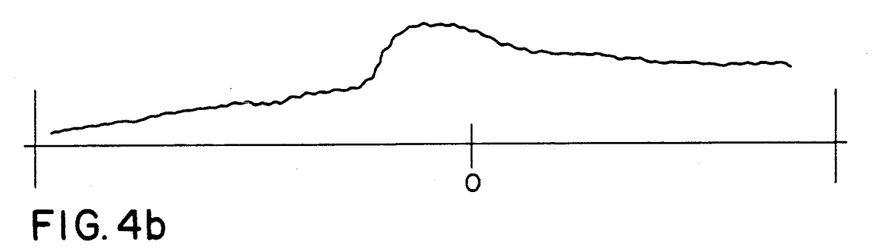

FIGS. 4A–4B illustrate the amplitude of reflected light, received from the receiver fiber 52 in the sensor as the sensor is advanced down through the introducer. In these figures, the horizontal axis corresponds to the distance the sensor has been moved down the introducer and the origin indicates the point at which the distal end of the sensor exits the introducer.

FIG. 4A shows the signal indicative of the amplitude of reflected infrared light, filtered through a 30 Hz low pass filter. In this view, it can be seen that the peak amplitude of the reflected light signal increases as the sensor approaches the distal end of the introducer, and then drops abruptly as the distal end of the sensor exits the introducer.

FIG. 4B shows a 0.1 Hz low pass filtered version of the signal illustrated in FIG. 4A. In this view, it can be seen that the same general pattern is followed by the low pass filtered signal, with the distal end of the sensor exiting the distal end of the introducer sensor shortly after the peak of the low pass filtered signal.

Figure 4C:
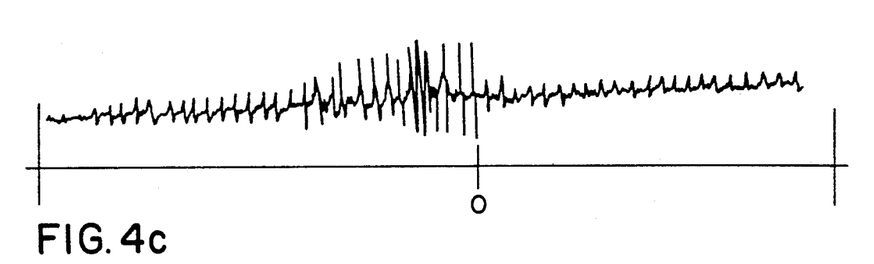

FIG. 4C shows a 5 Hz high pass filtered version of the signal illustrated in FIGS. 4A and 4B. In this drawing, it can be seen that the peak amplitude of the filtered signal increases until the sensor reaches the end of the introducer, and then abruptly decreases as the distal end of the sensor exits the introducer.

In FIGS. 4A, 4B and 4C, the signal indicative of the reflected light is a pulsatile signal, with pulses that correspond to the patient's heartbeat. As a result, the signal processing methods discussed below which analyze these signals, must take the pulsatile nature of the signals into consideration. The methods by which this is accomplished is discussed in more detail below.

The signals illustrated in FIGS. 4A, 4B and 4C can be used to monitor the position of the sensor as it passes through the introducer. A simple method of monitoring the sensor is to simply display the signal indicative of reflected light on a chart recorder of video display, and monitor its position by visual interpretation of the displayed signal. The apparatus illustrated in the article "A Fiber Optic Reflectance Oximeter", by Lansman et al, published in *Pflugers Archiv,* European Journal of Physiology, Springer-Verlag, 1978, pp. 273-282, and incorporated herein by reference, may be used to perform the method in this fashion. Preferably, however, an automatic system for monitoring the signals indicative of reflected light is incorporated into prior art reflectance oximeter monitoring apparatus.

Figure 5:
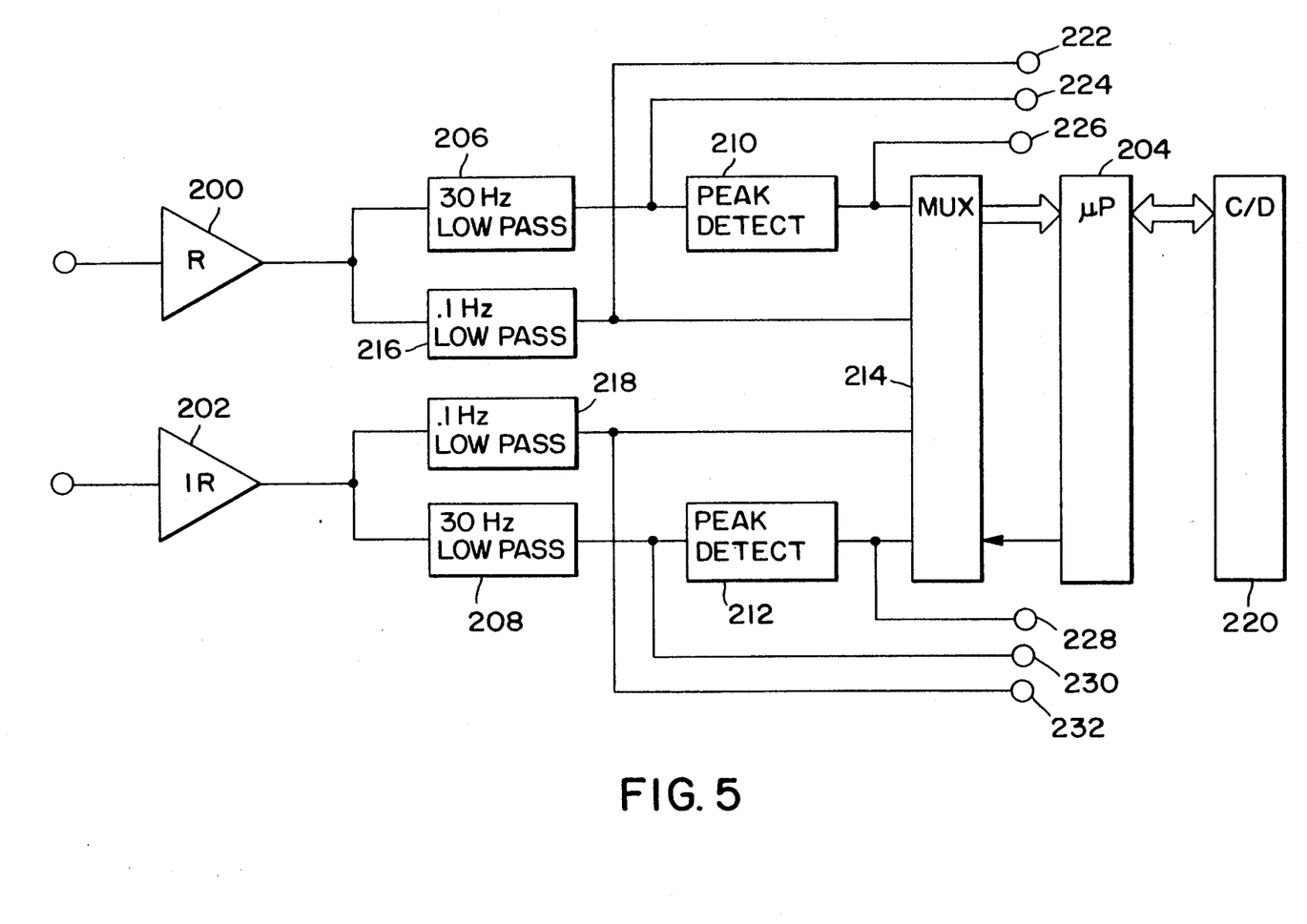
FIG. 5 is a functional schematic drawing of an apparatus appropriate for employing the method of the present invention.
Figure 6A:
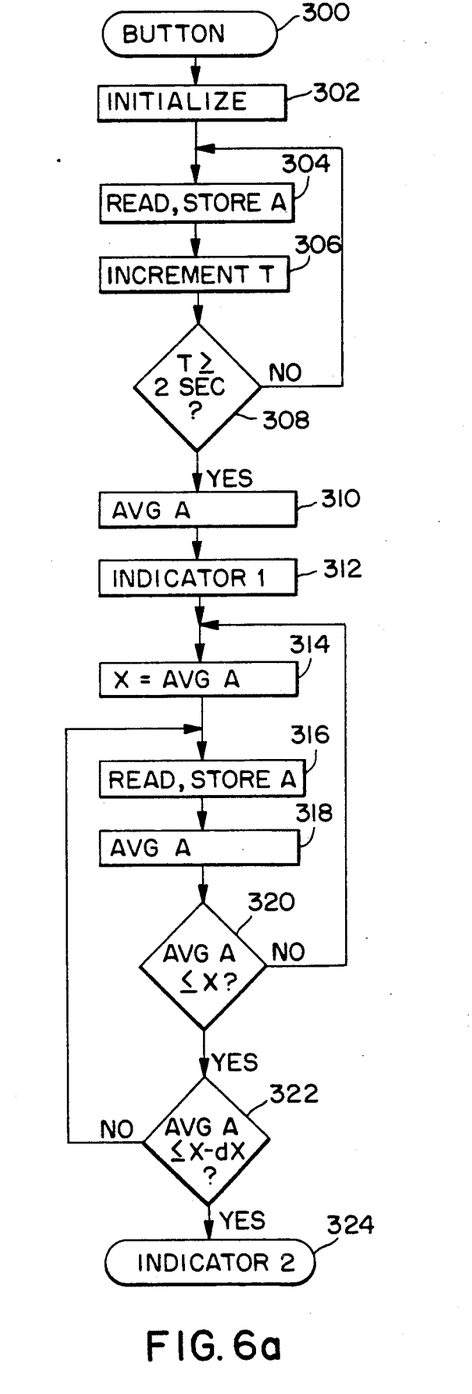
FIGS. 6A and 6B are flow charts illustrating the method of the present invention as it would be employed by an apparatus as illustrated in FIG. 5.
Figure 6B:
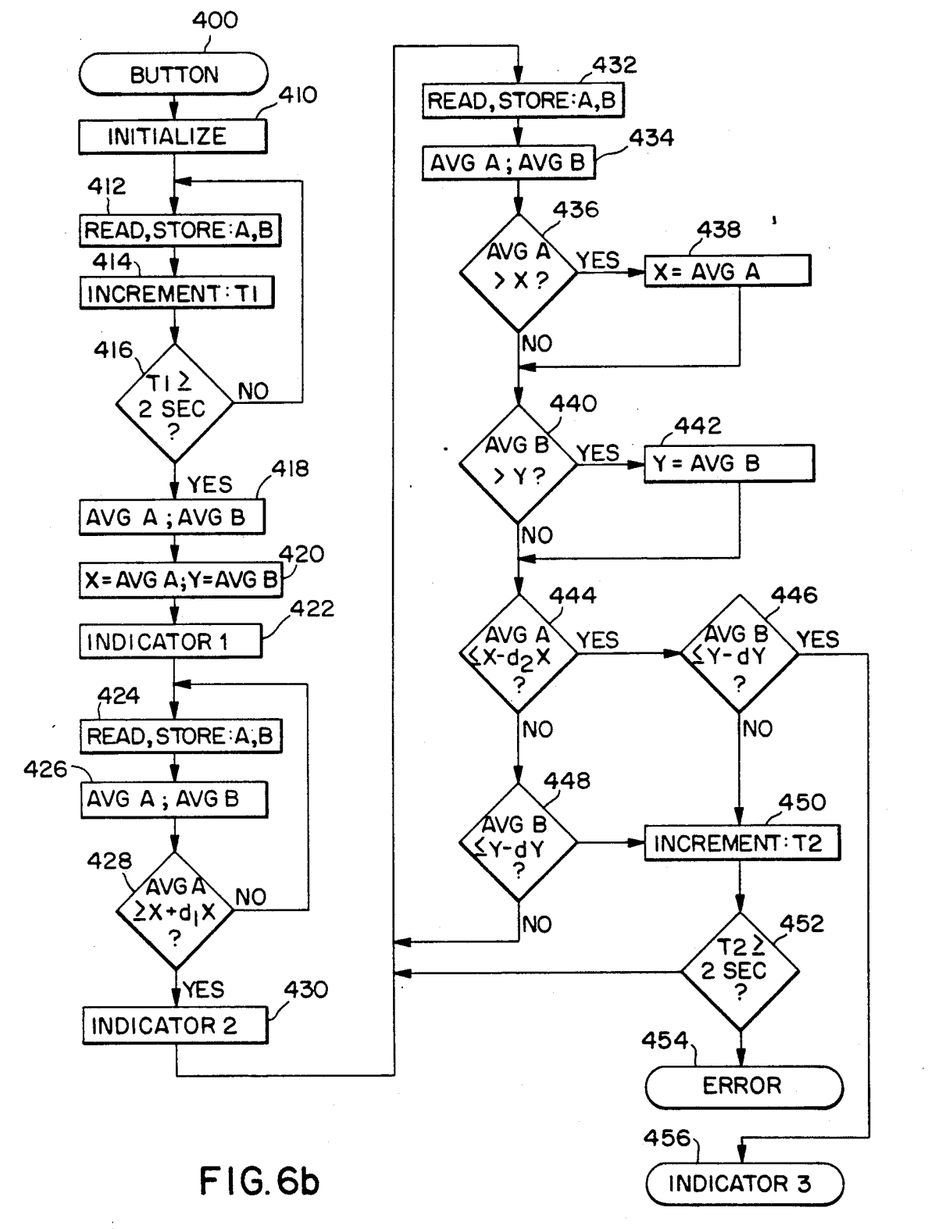

FIG. 5, in conjunction with the flow charts in FIGS. 6A and 6B, illustrates the way in which prior art monitors for reflectance oximeters may be modified to perform the method of the present invention. Physically, the apparatus is modified by providing filtration and peak detect stages intermediate the optical amplifiers 200, 202 which are to amplify reflected red and infrared light, respectively, and the signal analysis circuitry, microprocessor 204. In the event that only a single optical amplifier is used to amplify both red and infrared reflected light, the apparatus can be correspondingly simplified.

In addition to whatever other filtration and data processing functions are performed by the monitoring apparatus, signals indicative of reflected red or infrared light may be passed through either a peak detector or a low frequency (e.g. 0.1 Hz) low pass filter and provided to the data processing circuitry 204. As illustrated in FIG. 5, this may take the form of a microprocessor. A personal computer, with associated display and control apparatus 220, typically a CRT monitor and a keyboard, is believed to provide the simplest implementation at the present time.

As illustrated, FIG. 5 includes two different signal processing paths coupled to the output of each optical amplifier (200, 202). In the first signal processing path, the output of the optical amplifiers 200, 202 is passed through 30 Hz low pass filters 206 and 208, respectively, and then through peak detectors 210 and 212, before being provided to a signal multiplexer 214 so that they may be introduced to the data processor 204. The peak detectors 210 and 212 are preferably absolute magnitude peak detectors of the general type disclosed in U.S. Pat. No. 3,611,164, issued to Day, incorporated herein by reference in its entirety. Preferably, the peak detector effectively averages the peak value over several of the pulsatile cycles of the 30 Hz low pass filtered signals. The second signal path comprises passing the output of the optical amplifiers 200, 202 through 0.1 Hz low pass filters 216 and 218, respectively, prior to passing the signal through to the multiplexer 214.

FIG. 5 illustrates these additional signal processing stages coupled to the outputs of both the red and infrared amplifier. However, in order to practice the invention, it is only necessary that the additional signal processing be applied to one or the other of the signals indicative of the reflected levels of red or infrared light. As embodied by the inventors, the signals indicative of reflected infrared light have been used. However, monitoring reflected red light is workable as well. Either or both of the first and second signal processing paths may be used.

According to the flow charts illustrated in FIGS. 6A and 6B, microprocessor 204 analyzes the reflected signals and provides an output to a control/display 220. This may take the form of the CRT of a personal computer, a chart recorder, or other appropriate display mechanism. In addition, the device is illustrated as having external jacks 222, 224, 226, 228, 230 and 232 so that the signals, in their various stages of processing, may be applied directly to a display apparatus, without processing. In this case, the method of the present invention would be employed by the physician by inserting the sensor and visually monitoring the displayed signals directly, as discussed above.

With regard to a determination of the location of the end of the optical sensor relative to the introducer sensor, either signal processing path may be employed individually. However, it is believed preferable to combine the 30 Hz low pass/pea detected signal with the 0.1

Hz low pass filtered signal to provide a more accurate determination of the location of the end of the optical sensor. Furthermore, in this fashion, the two processed signals may be used to check one another's accuracy.

The operation of the an improved apparatus which may perform the method of the present invention is best understood in conjunction with the flow charts illustrated in FIGS. 6A and 6B. FIG. 6A illustrates a method intended to be used in conjunction with either the signal indicative of the amplitude of infrared reflected light, passed through the second processing path, 0.1 Hz low pass filter 218. In this case, the method is performed by introducing the sensor into the introducer after the introducer has been located in the venous system. After the sensor has been inserted into the introducer, the method is initiated by a button press 300 by the physician to indicate that the sensor has been inserted. Microprocessor 204 then initializes the system at 302, setting all stored values equal to 0. Stored values include A, which is indicative of the measured amplitude of the 0.1 Hz low pass filtered signal, AVG A, which is a running two second average of the values of the 0.1 Hz low pass filtered signal, T, which is s stored value incremented with each sample of the 0.1 Hz low pass filtered signal to function as a two second timer, and X, which is the peak recorded value of the 0.1 Hz low pass filtered signal.

After initialization, the multiplexer 214 is activated by the microprocessor 204 to repeatedly sample the output of low pass filter 218. The frequency of sampling may vary, however, a sampling frequencies greater than 100 Hz are believed to be workable in the context of the present invention.

The microprocessor 204 then accumulates two seconds of measured values of the 0.1 Hz low pass filtered signal by reading and storing at 304 and incrementing T at 306. This process continues until the value of T indicates that two seconds have passed at 308.

After the two second initial average has been taken, the control/display 22 indicates that the baseline has been established by means of a first indicator at 310. If the device takes the form of a personal computer based apparatus, the indicator can be a word or symbol flashed on the screen. Alternatively, the indicator may take the form of a flashing light or LED on a dedicated display.

After activation of the first indicator at 310, the microprocessor computes the running average AVG A of the readings taken over the previous two seconds to create an initial average at 312. The averaging function as used in this context and as used throughout the remainder of the description of this figure is an updated, running average of the data reflecting the previous two seconds. With each new reading of the amplitude of the reflected light, the oldest reading is deleted from the average, and the average is updated to reflect the new data added.

The flow chart illustrated includes a peak detection function. The value X is initially set equal to AVG A at 314, and is intended to reflect the recorded peak amplitude. As will be seen below, this average is updated as the value of the average level of the signal (AVG A) increases.

This microprocessor 204 next reads and stores the current value of the A 316, and this value is reflected in an updated average at 318. At 320, the average is checked against the previously recorded peak value X to determine whether a new peak value should be stored. If the then current running average (AVG A) is greater than X, X is set equal to AVG A. If not, AVG A is checked to see if it has dropped more than a certain amount (dX) from the recorded peak value X at 322. In the event that the average has dropped to a level more than dX below the previous recorded peak X, an indicator is activated at 324. This indicator allows the physician to determine that the end of the sensor has exited the introducer. In the event that the time out of the running average is not less than X-dX, the device continues to read, store and update AVG A until this condition is met.

as such, the method disclosed includes a software based peak detector coupled with a means for determining whether the signal has passed the peak. The value of dX is chosen to be greater than the pulsatile variations in the level of the signal obtained through the 0.1 Hz low pass filter 216 (FIG. 5). This prevents premature activation of the indicator.

While the method diagrammed in FIG. 6A is discussed as using the output of the second signal path (0.1 Hz low pass filter), the method may also be employed using the output of the peak detectors 210, 212 as inputs.

An alternative embodiment of the present invention employs both the 0.1 Hz low pass filtered signal and the 30 Hz low pass filtered signal passed through a peak detector. As illustrated in FIG. 4A and FIG. 4C, the peak value of the pulsatile signals drops off substantially after the distal end of the sensor exits the introducer. The method illustrated in FIG. 6B makes use of this fact in conjunction with the decrease in level of the low pass filtered signal to provide an indicator of the position of the fiber optic sensor. The two process signals are checked against one another as a safety measure.

Similar to the method illustrated in FIG. 6A, the method of FIG. 6B is initiated by a button push 400 by the physician, followed by initialization of the system, setting all values to 0 at 410. In this method, the values to be initialized include the amplitude of the 0.1 Hz low pass filtered signal, A; the amplitude of the output of the peak detector 212, B; first and second timer values $T_1$ and $T_2$; the stored maximum value of A, X; the stored maximum value of B, Y; and the two second running averages of A and B, which are designated AVG A and AVG B, respectively.

The amplitude of the 0.1 Hz low pass filtered signal (A) and the current value of the output of the peak detector 212, (B) are read and stored at 412. A timer T1 is incremented at 414 until its value indicates that two seconds of signals have been stored at 416. These stored signals are used to construct running, two second averages AVG A and AVG B at 418, and these running averages are used to set the initial values for X and Y at 420. After this initial averaging has been done, a first indicator 1 is activated at 422 to indicate to the physician that the sensor may now be advanced down the introducer.

Because there is a readily detectable increase in the value of the 0.1 Hz filtered signal as the sensor is moved down the introducer sensor, the method of FIG. 6B is adapted to detect when the signal passes a certain incremental change ($d_1X$) above the initial average value. The microprocessor 204 continues to read and store the values of both signals at 424 and to update the running average at 426. With each updated average, the microprocessor checks at 428 to determine whether the value of signal A has increased more than a predetermined amount $d_1X$ from the initial average value of X. If so, a second indicator is activated at 430, indicating to the physician that progress of the sensor down the introducer should be slowed, as the end of the sensor is near the end of the introducer. The microprocessor 204 continues to read and store the values of the two signals A and B at 432 and constructing the updated two second running averages at 434. The value of AVG A and AVG B are checked at 436 and 440, respectively, to determine whether they are greater than the previously recorded maximum values X and Y. If so, new maximum values are recorded at 438 and 442, respectively. Following these steps, the current value of AVG A is checked at 444 to determine whether it is less than the previously recorded maximum value X minus a predetermined value $d_2X$ which would indicate that the fiber optic sensor had exited the introducer sensor. If so, the current value of AVG B is checked at 446 to determine whether it is less than the previous maximum value Y minus a predetermined value dY. If both signals are significantly less than their recorded maximum levels, thus confirming one another, a third indicator is lit at 456 to inform the physician to cease advancing the fiber optic sensor down the introducer sensor.

In the event that the value of AVG A is not less than the $X-d_2X$, the value of AVG B is compared with its previously recorded peak to determine whether it is less than Y-dY at 448. If AVG A and AVG B do not produce concurring results, that is one indicates that the fiber optic sensor has exited the end of the introducer sensor and the other does not, a second timer T2 is incremented at 450. If the disagreement continue for two seconds, as checked at 452, an error signal 454 is produced to indicate to the physician that the insertion process should be restarted.

The values for dX, $d_1X$, $d_2X$ and dY will vary depending upon the particular fiber optic sensor system employed, and upon the particular introducer employed. Therefore, before employing the method of the present invention, it may be necessary to calibrate the monitoring system to the particular sensor type employed to set the appropriate values for dX, $d_1X$, $d_2X$ or dY. As a practical matter, it is believed that with regard to dX as used in the method illustrated in FIG. 6A and $d_2X$ as used in the method of FIG. 6B, a value of approximately 20% of the stored maximum value X is appropriate. Similarly, the value of dY and the method of FIG. 6B may conveniently be approximately 20% of the recorded maximum value Y. With regard to the value of $d_1$ as employed in the algorithm of FIG. 6B, it is suggested that $d_1$ be roughly equal to the initial value of X set after the initial two second monitoring period. In any case, it is believed that as physicians become used to the procedure, they may wish to optimize the response to the system by varying these parameters according to their own emperical experience, and to reflect the speed at which they prefer to advance the sensor down the introducer.

Figure 7:
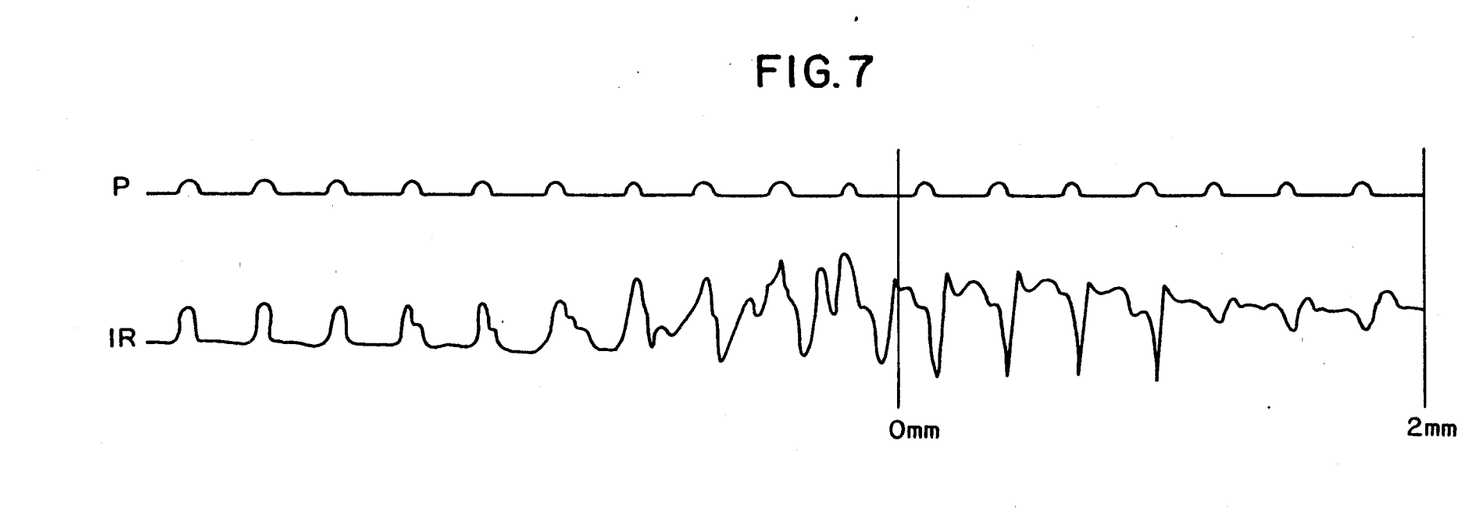
FIG. 7 illustrates a comparison of a blood pressure tracing and the signal indicative of light reflected into the distal end of the sensor as it passes down the introducer.

FIG. 7 shows a comparison of a blood pressure tracing (upper tracing) and a tracing of the signal indicating light reflected back into the distal end of the sensor (lower tracing). The peaks in the upper tracing correspond to the peak pressure during contraction of the heart. In these tracings, the sensor exits the introducer at the point marked "0 mm". An examination of the tracings of FIG. 7 reveals that the relative phase of the two signals changes as the sensor passes down the introducer. While the sensor is within the introducer, the positive peaks of both signals are in phase with one another. As the fiberoptic sensor approaches the distal end of the introducer, the relative phase of the reflected light signal shifts. By the time the optical sensor has emerged 2 mm from the distal end of the introducer, the positive peaks of the pressure signal are in almost exact phase to the negative peaks of the reflected light signal. The apparatus in FIG. 8 is constructed to take advantage of this behavior in order to provide an indication of appropriate sensor positioning.

Figure 8:
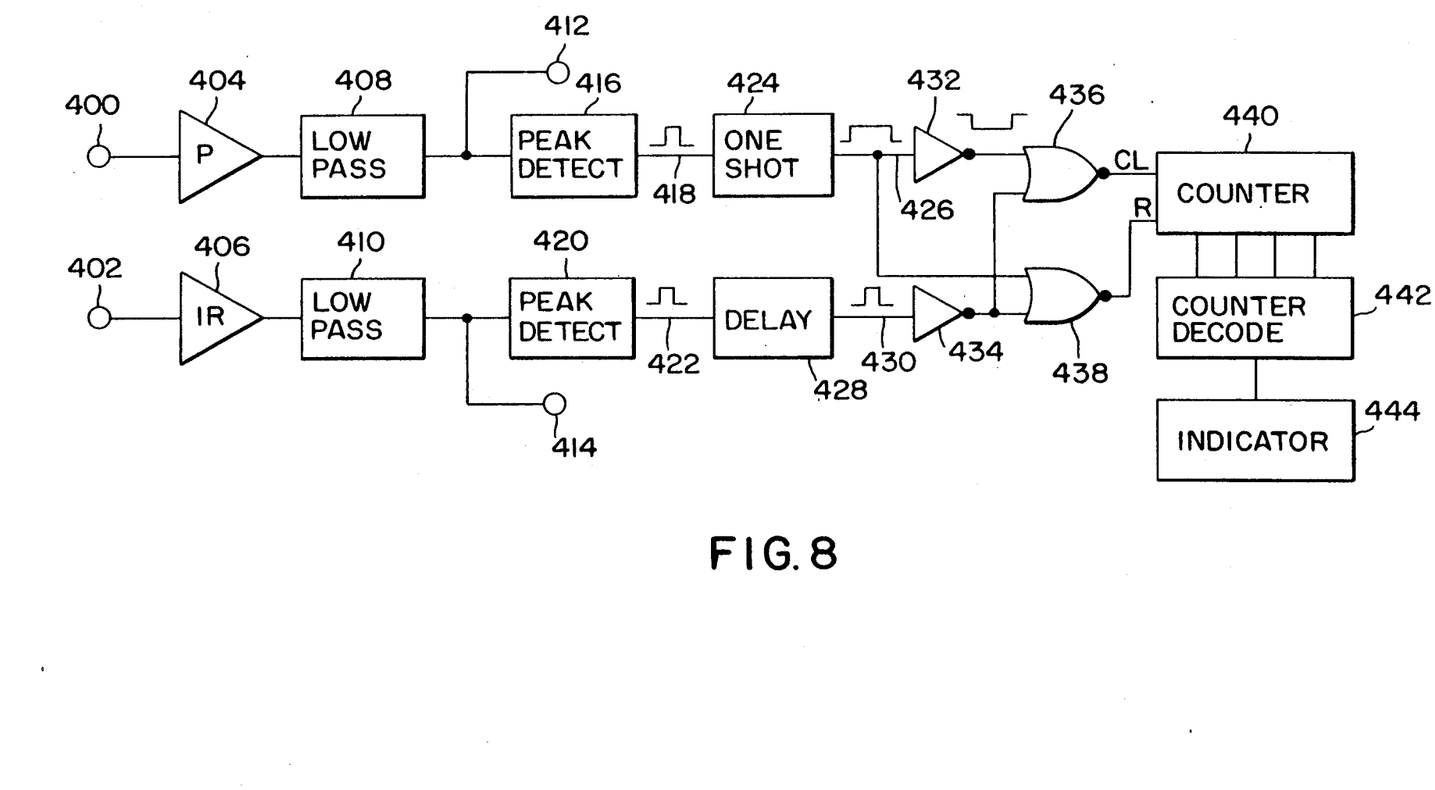
FIG. 8 is a functional schematic drawing of another embodiment of an apparatus appropriate for employing the method of the present invention.

FIG. 8 is a functional diagram of an apparatus appropriate for detecting the phase change illustrated in FIG. 7. Blood pressure and reflected light signals are applied to the apparatus at connectors 400 and 402, respectively. The signals are amplified by amplifiers 404 and 406 and passed through a low pass filters 408 and 410. Low pass filters 408 and 410 may be 30 Hz low pass filters of the type described in conjunction with the apparatus illustrated in FIG. 5 above. The output of low pass filters 408 and 410 corresponds generally to the simulated tracings illustrated in FIG. 7. In some cases, it may be desirable to provide output jacks 412 and 414 so that this information can be applied to a strip recorder. The examination of the displayed signals may be used to identify the phase shift referred to above, if this is convenient for the physician. Alternatively, the remainder of the apparatus of FIG. 8 may be employed to detect the phase change.

The low pass filtered pressure signal is applied to a peak detector 416 which generates a 1 ms pulse on line 418 indicating the occurrence of the positive blood pressure peak. The low pass filtered reflected light signal is applied to a peak detector 420, which generates a 1 ms pulse on line 422 indicative of the detection of a negative peak in the filtered reflected light signal.

The remainder of the circuitry of FIG. 8 compares the relative timing of the peak detect pulses on line 418 and 422. The peak detect pulse on line 408 triggers a one-shot 424 which generates a positive pulse of approximately 30 ms duration on line 426. The negative peak detect pulse on line 422 is provided to a delay 428 which generates a 1 ms pulse on line 430, 15 ms thereafter.

Comparison logic including inverters 432 and 434 and NOR gates 436 and 438 is used to determine whether the pulse on line 430 occurs concurrent with the pulse on line 426, which would indicate occurrence of a negative peak in the reflected light signal within 15 ms of the positive peak in the pressure signal. If this occurs, counter 440 is closed. If the negative peak occurs outside of these bounds, counter 440 is reset. Counter decode 442 activates indicator 444 in response to counter 440 reaching a count indicative of the occurrence of a predetermined number of successive number of negative reflected light peaks in phase with the positive peaks in the pressure signal. This predetermined number will vary depending on the specifics of the sensor system used, however, a count of at least 3 or 4 is believed desirable in order to prevent premature activation of indicator 444.

In order for the apparatus of FIG. 8 to function properly, it is important that the sensor be advanced slowly down the introducer sensor when it is in the general vicinity of the distal end of the introducer sensor, in order to allow for detection of the phase change before the sensor has exited a significant distance from the distal end of the introducer. The number of sequentially counted in phase events required to activate indicator 444 may be adjusted in order to reflect the physician's preferred speed of introduction of the sensor.

In order to practice the method of the present invention, it is important that the introducer sensor be flushed clean of any blood, prior to insertion of the fiber optic sensor. In the event that the procedure must be restarted, it is similarly necessary to reflush the introducer sensor and to flush the surface of the fiber optic sensor to prevent blood located within the introducer sensor from interferring with the proper location of the fiber optic sensor.

While the invention is disclosed in the context of a microprocessor based device, it is also believed that it may be practiced using dedicated circuitry as an alternative. In addition, while it is envisioned that in the context of a microprocessor based system, the various indicators employed will take the form of screen displays, in the context of a system employing dedicated circuitry, the indicators could be one or more of a series of LED's, indicating the various stages of advancement of the fiber optic sensor, down the introducer sensor.

As such, the above implementation should be considered exemplary, rather than limiting with regard to the claims that follow.

We claim:

1. An apparatus for monitoring insertion of a fiber optic sensor of a type which functions by emission of light into a body and reception of light reflected from the body, through an introducer, into a blood vessel, comprising:
   monitoring means for monitoring light received by said sensor and for generating a signal indicative of an amount of light received by said sensor; and
   means for monitoring signals having positive and negative peaks indicative of heart contractions and for comparing the positive peaks of said signals indicative of heart contractions with negative peaks of said signals indicative of light received by said sensor in order to determine the relative positions of said sensor and said introducer.

2. A method according to claim 1 wherein said analyzing step comprises generating an electrical signal indicative of said light received by said sensor, filtering said electrical signal to remove low frequency components and detecting a peak level of said filtered electrical signal to provide an indication that the distal end of said sensor has exited the distal end of said introducer.

3. A method according to claim 1 wherein said analyzing step comprises generating an electrical signal indicative of said light received by said sensor, filtering said electrical signal to remove high frequency components and detecting a peak amplitude of said filtered electrical signal to provide an indication that the distal end of said sensor has exited the distal end of said introducer.

4. An apparatus for monitoring insertion of a fiber optic sensor having a distal end of a type which functions by emission of light into a body and reception of light reflected from the body, through an introducer having a distal end, into a blood vessel, comprising:
   monitoring means for monitoring light received by said sensor and for generating a signal indicative of an amount of light received by said sensor; and
   means for analyzing said signal indicative of light received by said sensor to determine a relative position of said sensor with respect to said introducer and for providing an indication of said relative position of said sensor and said introducer wherein said analyzing means comprises a filtration means for filtering said signal indicative of light received by said sensor to remove low frequency components and a peak detection means for detecting the peak amplitude of said filtered electrical signal, to provide an indication that the distal end of said sensor has exited the distal end of said introducer.

5. An apparatus for monitoring insertion of a fiber optic sensor of a type which functions by emission of light into a body and reception of light reflected from the body, through an introducer, into a blood vessel, comprising:
   monitoring means for monitoring light received by said sensor and for generating a signal indicative of an amount of light received by said sensor; and
   means for analyzing said signal indicative of light received by said sensor to determine a relative position of said sensor with respect to said introducer and for providing an indication of said relative position of said sensor and said introducer wherein said analyzing means comprises a filtration means for filtering said signal indicative of light received by said sensor to remove high frequency components and a peak detection means for detecting the peak amplitude of said filtered signal to provide an indication that the distal end of said sensor has exited the distal end of said introducer.

6. A method of insertion of a fiber-optic sensor of the type which functions by emission of light into the body and the reception of light reflected from the body, comprising:
   inserting an introducer with a distal end into a blood vessel;
   introducing said sensor with a distal end into said introducer;
   coupling said sensor to monitoring equipment for monitoring light received by said sensor;
   advancing said sensor through said introducer while monitoring said light received by said sensor and analyzing said light received by said sensor to determine a relative position of said sensor with respect to the distal end of said introducer; and
   ceasing introduction of said sensor when said analysis of said light received by said sensor indicates that the distal end of said sensor has exited the distal end of said introducer.

7. A method according to claim 1 wherein the step of introducing said sensor comprises introducing a reflectance oximeter sensor comprises a reflectance oximeter sensor.

8. A method according to claim 1 or claim 2 wherein said analysis of said light received by said sensor comprises the step of determining the position of maximum amplitude of said light received by said sensor in order to identify the position at which the distal end of said sensor emerges from the distal end of said introducer.

9. A method according to claim 1 wherein said method further comprises monitoring a signal including positive peaks and negative peaks indicative of a heart contractions of the patient in whom said sensor is to be implanted and comparing relative timing of the positive peaks of said signal indicative of the heart contractions of said patient with the negative peaks of the signal indicative of light received by said sensor in order to determine the position at which the distal end of said sensor exits the distal end of said introducer.

* * * * *

UNITED STATES PATENT AND TRADEMARK OFFICE
CERTIFICATE OF CORRECTION

PATENT NO. : 5,168,873
DATED : December 8, 1992
INVENTOR(S) : George P. Seifert, Jeffrey A. Schweitzer, and Jerome T. Hartlaub It is certified that error appears in the above-indentified patent and that said Letters Patent is hereby corrected as shown below:

Column 3, Line 14, delete "indicator", and insert in its place --introducer--.

Column 3, Line 56, delete "of", and insert in its place --or--.

Column 4, Line 68, delete "pass/pea", and insert in its place --pass/peak--.

Column 5, Line 23, delete "s stored", and insert in its place --a stored--.

Column 8, Line 49, delete "closed", and insert in its place --clocked--.

Column 10, Line 11, after "introducer", add --having a distal end--.

Column 10, Line 35, after "introducer", add --with a distal end--.

Column 10, Lines 48-49, delete "a reflectance oximeter sensor comprises",

Signed and Sealed this

Fourth Day of October, 1994

Attest:

BRUCE LEHMAN

*Attesting Officer*     *Commissioner of Patents and Trademarks*